United States Patent [19]

Acker et al.

[11] 4,353,732
[45] Oct. 12, 1982

[54] 3,4,5,6-TETRAHYDRO-1,2,4,6-THIATRIAZINE-3,5-DIONE-1,1-DIOXIDES; PROCESSES FOR CONTROLLING UNDESIRED PLANT GROWTH

[75] Inventors: Rolf-Dieter Acker, Leimen; Gerhard Hamprecht, Weinheim; Adolf Parg, Bad Duerkheim; Bruno Wuerzer, Otterstadt, all of Fed. Rep. of Germany

[73] Assignee: BASF Aktiengesellschaft, Fed. Rep. of Germany

[21] Appl. No.: 247,983

[22] Filed: Mar. 26, 1981

[30] Foreign Application Priority Data

Apr. 5, 1980 [DE] Fed. Rep. of Germany ....... 3013268

[51] Int. Cl.³ .................... A01N 43/72; C07D 285/00
[52] U.S. Cl. ........................................... 71/91; 544/7
[58] Field of Search ............................... 71/91; 544/7

[56] References Cited

U.S. PATENT DOCUMENTS

| | | | |
|---|---|---|---|
| 3,313,811 | 4/1967 | Becke | 544/7 |
| 3,435,031 | 3/1969 | Whitehead | 544/7 |
| 3,817,993 | 6/1974 | Franke | 260/243 |
| 3,856,786 | 12/1974 | Huber | 544/7 |

*Primary Examiner*—John M. Ford
*Attorney, Agent, or Firm*—Keil & Witherspoon

[57] ABSTRACT

3,4,5,6-Tetrahydro-thiatriazine-3,5-dione-1,1-dioxides of the formula

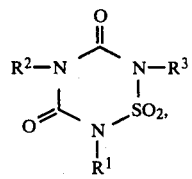

I where $R^1$, $R^2$ and $R^3$ have the meanings given in the main text, which possess herbicidal properties.

3 Claims, No Drawings

3,4,5,6-TETRAHYDRO-1,2,4,6-THIATRIAZINE-3,5-DIONE-1,1-DIOXIDES; PROCESSES FOR CONTROLLING UNDESIRED PLANT GROWTH

The present invention relates to novel 3,4,5,6-tetrahydro-1,2,4,6-thiatriazine-3,5-dione-1,1-dioxides, processes for their preparation, herbicides which contain these compounds as active ingredients, and processes for controlling undesired plant growth by means of these compounds.

U.S. Pat. No. 3,435,031 describes substituted 3,4,5,6-tetrahydro-1,2,4,6-thiatriazine-3,5-dione-1,1-dioxides as bactericides, fungicides and fly repellants. A herbicidal action of these compounds has not previously been disclosed.

We have found thiatriazine derivatives which possess a herbicidal action. Accordingly, the present invention relates to 3,4,5,6-tetrahydro-thiatriazine-3,5-dione-1,1-dioxides of the formula I

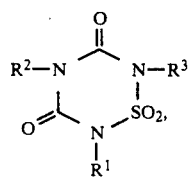

where $R^1$ is hydrogen, a metal atom, an unsubstituted or substituted ammonium radical, a saturated or unsaturated straight-chain aliphatic radical of up to 10 carbon atoms, a cycloaliphatic radical of 3 to 7 carbon atoms, a branched saturated or unsaturated aliphatic radical of 3 to 10 carbon atoms or an unsubstituted or halogen-substituted benzyl radical, $R^2$ has the same meanings as $R^1$ or is a halogen-, alkyl-, haloalkyl-, alkoxy-, haloalkoxy-, alkylthio-, haloalkylthio- or haloalkylsulfonyl-substituted phenyl radical of up to 10 carbon atoms and $R^3$ is a saturated or unsaturated straight-chain aliphatic radical of up to 10 carbon atoms, a cycloaliphatic radical of 3 to 7 carbon atoms, a branched saturated or unsaturated aliphatic radical of 3 to 10 carbon atoms, an unsubstituted or halogen-substituted benzyl radical, or a halogen-, alkyl-, haloalkyl, alkoxy-, haloalkoxy-, alkylthio-, haloalkylthio- or haloalkylsulfonyl-substituted phenyl radical of up to 10 carbon atoms, but $R_2$ and $R^3$ are not both saturated straight-chain aliphatic radicals or benzyl radicals.

$R^1$ and $R^2$ may be, for example, sodium, potassium, ammonium, dimethylammonium, tridecylammonium, trimethylammonium, diisopropylethylammonium, diisopropylmethylammonium or N-methyl-N,N-diethanolammonium.

$R^2$ and $R^3$ may be, for example, methyl, ethyl, propyl, isopropyl, cyclopropyl, butyl, isobutyl, sec.-butyl, tert.-butyl, pentyl, cyclopentyl, hexyl, cyclohexyl, 3-pentyl, 1,2-dimethylpropyl, 1,3-dimethylbutyl, 2-chloroethyl, 2-chloropropyl, 3-chloropropyl, 2-chloroisopropyl, 1-chloromethylpropyl, 1-ethyl-2-methylpropyl, 1,2,2-trimethylpropyl, 1,2-dimethylhexyl, 1-cyclohexylethyl, 2-chlorobut-3-yl, 2-chloro-2-methylpropyl, 2-fluorobut-3-yl, 2-fluoro-2-methylpropyl, 2-fluoroisopropyl, tert.-amyl, chloro-tert.-butyl, 2,2,2-trifluoroethyl, methoxyethyl, ethoxyethyl, 3-methoxypropyl, methoxyisopropyl, 3-methoxybutyl, 1-methoxybut-2-yl, ethoxy-tert.-butyl, methoxy-tert.-butyl, 2-methoxybutyl, 4-methoxybutyl, allyl, methallyl, crotyl, 2-ethylhex-2-en-1-yl, hex-5-en-1-yl, 2-methylbut-2-en-1-yl, 2-methylbut-1-en-3-yl, but-1-yn-3-yl, but-2-yn-1-yl, but-1-en-3-yl, propargyl, 2-methylbut-1-en-4-yl, 2-methylbut-2-en-4-yl, 3-methylbut-1-en-3-yl, methylmercaptoethyl, ethylmercaptoethyl, 3-methylmercaptopropyl, 3-methylmercaptobutyl, 1-methylmercaptobut-2-yl, methylmercaptotert.-butyl, 2-methylmercaptobutyl, cyclohexoxyethyl, benzyl, 2,6-dichlorobenzyl, 2-chloro-6-fluorobenzyl or 2,6-difluorobenzyl.

Halogen is fluorine, chlorine, bromine or iodine.

In addition, $R^2$ and $R^3$ may be, for example, o-, m- and p-chlorophenyl, o-, m- and p-fluorophenyl, o-, m- and p-bromophenyl, 2,3-, 2,4-, 2,5-, 2,6-, 3,4- and 3,5-dichlorophenyl, 2,4,5-trichlorophenyl, 3,4-difluorophenyl, 3-chloro-4-fluorophenyl, 3-fluoro-4-chlorophenyl, o-, m- and p-methoxy-, o-, m- and p-ethoxy-, o-, m- and p-isopropoxy, o-, m- and p-trifluoromethoxy-, o-, m- and p-methyl-, o-, m- and p-ethyl-, o-, m- and p-propyl-, o-, m- and p-isopropyl-, o-, m- and p-isobutyl-, o-, m- and p-tert.-butyl-, o-, m- and p-methylthio-, o-, m- and p-trichloromethylthio-, o-, m- and p-trifluoromethylthio-, o-, m- and p-trifluoromethyl-, o-, m- and p-difluoroethyl-, o-, m- and p-trifluoroethyl-, o-, m- and p-tetrafluoroethyl-, o-, m- and p-pentafluoroethyl-, o-, m- and p-trifluoromethylsulfonyl-, 3-chloro-4-methoxy-, 3-chloro-4-bromo- and 3-chloro-4-methyl-phenyl.

The novel compounds of the formula I may be prepared by, (a) if $R^1$ is hydrogen, reacting an N-aryl-N'-alkyl-urea of the formula II

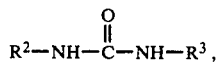

where $R^2$ and $R^3$ have the above meanings, with chlorosulfonyl isocyanate, in the presence or absence of an acid acceptor and of an inert solvent, at from −40° to 100° C., or (b) if $R^2$ is hydrogen, reacting a sulfonediamide of the formula III $$R^1-NH-SO_2-NH-R^3 \quad \text{III},$$

where $R^1$ and $R^3$ have the above meanings, with chlorocarbonyl isocyanate, in the presence or absence of an acid acceptor and of an inert organic solvent, at from 0° C. to 150° C., or (c) reacting a urea of the formula II

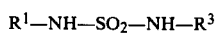

or a urea of the formula IV $$R^2-NH-CO-NH_2 \quad \text{IV},$$

where $R^2$ and $R^3$ have the above meanings, with a sulfamyl chloride of the formula V

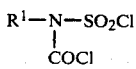

or a sulfamyl chloride of the formula VI $$R^1-N-SO_2Cl \atop |\phantom{xx}CO_2R^4,} \quad \text{VI}$$

where $R^1$ has the above meanings, with the exception of hydrogen, a metal atom or an ammonium radical, and $R^4$ is alkyl or cycloalkyl of up to 6 carbon atoms, in the presence or absence of an acid acceptor and of an inert solvent, at from $-20°$ to $100°$ C., or (d) reacting a sulfonediamide of the formula III with a carbamyl chloride of the formula VII $$R^2-N-CO-OR^4 \atop |\phantom{xx}CO-Cl} \quad \text{VII}$$

or a carbamyl chloride of the formula VIII $$R^2-N-CO-Cl \atop |\phantom{xx}CO-Cl} \quad \text{VIII}$$

where $R^2$ and $R^4$ have the above meanings, with the exception of hydrogen, a metal atom or an ammonium radical, in the presence or absence of an acid acceptor and of an inert solvent, at from $-20°$ C. to $100°$ C., or (e) if $R^2$ is hydrogen, reacting a sulfamyl chloride of the formula IX $$R^1-N-SO_2Cl \atop |\phantom{xx}CO-NCO,} \quad \text{IX}$$

where $R^1$ has the above meanings, with the exception of hydrogen, a metal atom and an ammonium radical, with an amine of the formula X $$R^3-NH_2 \quad \quad \quad \text{X,}$$

where $R^3$ has the above meanings, in the presence or absence of an acid acceptor and of an inert solvent, at from $-100°$ C. to $100°$ C., and, in each case, converting the compound obtained, if desired, into a salt and/or, if $R^1$ and/or $R^3$ is hydrogen, alkylating the compound obtained.

Process (a) can be represented by the following equation:

$$R^2-NH-CO-NH-R^3 +$$

II $$Cl-SO_2-NCO \xrightarrow{-HCl}$$

[structure I: six-membered ring with $R^2-N$, $C=O$, $N-R^3$, $SO_2$, $N-H$, $C=O$]

I

The starting materials are employed in about the stoichiometric ratio, ie. using from 0.8 to 1.2 moles of chlorosulfonyl isocyanate per mole of II. Where appropriate, an acid acceptor can be added to assist completion of the reaction.

The fact that the reaction takes place in a single regio-specific manner is surprising. In spite of the high reactivity of chlorosulfonyl isocyanate, the presence of two amide nitrogens and the well-known sulfonation of anilines (J. Chem. Soc. Perkin I (1979), 1,043), neither sulfonation of the second nitrogen nor sulfonation of the aryl nucleus occur under the stated reaction conditions.

The process is advantageously carried out by running the chlorosulfonyl isocyanate into a mixture of the urea of the formula II and an inert solvent at from $-40°$ C. to $100°$ C., preferably from $-20°$ C. to $40°$ C. Where appropriate, the acid acceptor can be added, in an amount of from 0.5 to 1.5 equivalents, after from 0.5 to 48 hours, preferably from 1 to 12 hours, at from $-20°$ C. to $40°$ C. To complete the reaction, the mixture is stirred for from 0.5 to 48 hours, preferably from 2 to 12 hours, at from $-20°$ C. to $80°$ C. The reaction mixture is then concentrated. The desired end products of the formula I can be isolated in a pure form by reprecipitation, recrystallization or precipitation as salts, and can, if desired, be purified further by chromatography.

Process (b) can be represented by the equation:

$$R^1-NH-SO_2-NH-R^3 + Cl-CO-NCO \longrightarrow$$

III

[structure I: six-membered ring with $R^2-N$, $C=O$, $N-H$, $SO_2$, $N-R^1$, $C=O$]

I

The starting materials are employed in about the stoichiometric ratio, ie. using from 0.8 to 1.2 moles of chlorocarbonyl isocyanate per mole of III. Where appropriate, an acid acceptor can be added to assist completion of the reaction.

The smooth formation of a triazinone system by an intramolecular mechanism from chlorocarbonyl isocyanate and sulfonediamides is surprising, since, given the reactivity of chlorocarbonyl isocyanate, it might be expected that intramolecular linking reactions between the two trifunctional systems would predominate. In this light, the formation of a regio-specific product is particularly surprising.

The process is advantageously carried out by running the chlorocarbonyl isocyanate into a mixture of the sulfonediamide III and an inert solvent at from $0°$ to $150°$ C., preferably at from $10°$ to $50°$ C. If appropriate, an acid acceptor, in an amount of from 0.5 to 1.5 equivalents, can be added after from 0.5 to 24 hours, preferably from 1 to 12 hours, at from $0°$ C. to $40°$ C. To complete the reaction, the mixture is stirred for from 1 to 48 hours, preferably from 2 to 12 hours, at from $80°$ C. to $130°$ C. After filtering the mixture, the desired end products of the formula I can be obtained by precipitation or by concentrating the reaction mixture; if desired, they can be purified by recrystallization or chromatography.

Process (c) can be represented by the following equations:

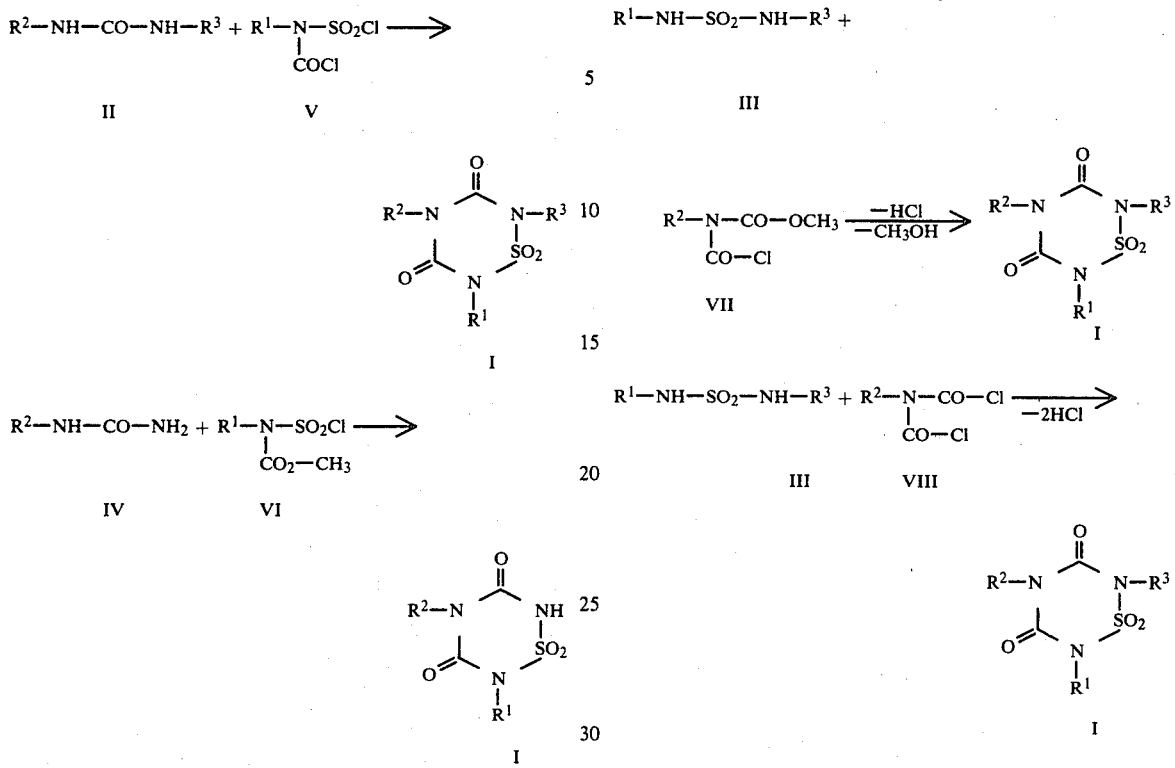

The starting materials II and V, and IV and VI, respectively, are employed in about the stoichiometric ratio, ie. using from 0.8 to 1.2 moles of starting material II or IV per mole of V or VI respectively.

The process is advantageously carried out by running the chloride V or VI and the equivalent amount of acid acceptor, from two separate feeds, into an about equivalent amount of urea of the formula IV in an inert solvent at from −20° C. to 100° C., preferably from 0° to 40° C. The mixture is then stirred for from 2 to 24 hours at from 0° to 100° C., preferably from 20° to 60° C.

If sulfamyl chlorides of the formula V are used, the mixture is concentrated if appropriate or, in the case of water-immiscible solvents, is extracted with dilute hydrochloric acid to remove the hydrochlorides. The desired end products of the formula I can then be purified, if desired, by recrystallization or chromatography.

If sulfamyl chlorides of the formula VI are used, the cyclization can, if appropriate after separating off the hydrochlorides, be effected in the presence of from an equal amount to a 2.5-fold amount of base, or in an organic medium in the presence of from an equal amount to a 2.5-fold amount of alcoholate, at from −20° C. to 100° C., preferably from 20° C. to 80° C. To work up the end products of the formula I, the mixture is then acidified and the precipitate formed is filtered off, where necessary after first concentrating the mixture. The desired end products are thus obtained in a pure form, but can, if desired, be purified further by recrystallization or chromatography.

Process (d) takes place in accordance with the following equations:

The starting materials III and VII or VIII are employed in about the stoichiometric ratio, ie. using from 0.8 to 1.2 moles of starting material III per mole of VII or VIII.

The process is advantageously carried out by running the carbamyl chloride VII or VIII and the equivalent amount of acid acceptor, from two separate feeds, into an about equivalent amount of sulfonediamide of the formula III in an inert solvent at from 20° C. to 100° C., preferably from 0° to 40° C. The mixture is then stirred for from 2 to 24 hours at from 0° to 100° C., preferably from 20° to 60° C., to complete the reaction.

If carbamyl chlorides of the formula VIII are used, the reaction mixture is concentrated if appropriate or, in the case of water-immiscible solvents, is extracted with dilute hydrochloric acid to remove the hydrochlorides. The desired end products of the formula I can then be purified, if desired, by recrystallization or chromatography.

If carbamyl chlorides of the formula VII are used, the cyclization can, if appropriate after separating off the hydrochlorides, be effected in the presence of from an equal amount to a 2.5-fold amount of base, or in an organic medium in the presence of from an equal amount to a 2.5-fold amount of alcoholate, at from −20° C. to 100° C., preferably from 20° C. to 80° C. To work up the end products of the formula I, the mixture is then acidified and the precipitate formed is filtered off, where necessary after first concentrating the mixture. The desired end products are thus obtained in a pure form, but can, if desired, be purified further by recrystallization or chromatography.

Reaction (e) takes place as follows:

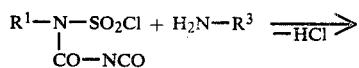

IX      X

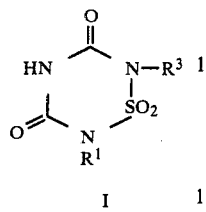

I

The starting materials IX and X are employed in about the stoichiometric ratio, ie. using from 0.8 to 1.2 moles of starting material IX per mole of X.

The process is advantageously carried out by running the amine X, where appropriate in an inert solvent, into a solution of the sulfamyl chloride IX in an inert solvent at from $-100°$ C. to $50°$ C., preferably from $-80°$ C. to $0°$ C. To complete the reaction, the mixture can subsequently be stirred for from 0.5 to 24 hours, preferably from 1 to 12 hours, at from $0°$ C. to $100°$ C., preferably from $20°$ C. to $80°$ C.

To isolate the end products of the formula I, the precipitate is filtered off or the reaction mixture is concentrated, if appropriate. The thiatriazine I can then be obtained pure by adding from an equal to a 2.5-fold amount of a base and subsequently acidifying the mixture; where appropriate, the product can also additionally be purified by recrystallization or chromatography.

The subsequent alkylation of the compounds obtained in which $R^1$ and/or $R^2$ is hydrogen can be carried out with the corresponding alkyl halides or dialkyl sulfates. Amongst these, methyl iodide and dimethyl sulfate are preferred.

The alkylation is advantageously carried out by running the alkylating agent into the compound of the formula I ($R^1=H$ or $R^2=H$), in the presence or absence of an acid acceptor, in an inert solvent at from $0°$ C. to $100°$ C., preferably from $10°$ C. to $40°$ C. The mixture is then additionally stirred for from 2 to 24 hours at from $0°$ C. to $100°$ C., preferably at from $20°$ C. to $60°$ C.

The end products of the formula I can, where required, be isolated in a pure form by precipitation, or by concentrating the solution and recrystallizing the residue, or by chromatography.

The processes according to the invention can be carried out continuously or batchwise, under atmospheric or superatmospheric pressure; for simplicity, atmospheric pressure is preferred.

The processes according to the invention are carried out in organic solvents which are inert under the particular reaction conditions. Examples of suitable solvents include halohydrocarbons, especially chlorohydrocarbons, eg. tetrachloroethylene, 1,1,2,2- or 1,1,1,2-tetrachloroethane, dichloropropane, methylene chloride, dichlorobutane, chloroform, chloronaphthalene, dichloronaphthalene, carbon tetrachloride, 1,1,1- or 1,1,2-trichloroethane, trichloroethylene, pentachloroethane, o-, m- and p-difluorobenzene, 1,2-dichloroethane, 1,1-dichloroethane, 1,2-cis-dichloroethylene, chlorobenzene, fluorobenzene, bromobenzene, iodobenzene, o-, p- and m-dichlorobenzene, o-, p- and m-dibromobenzene, o-, m- and p-chlorotoluene and 1,2,4-trichlorobenzene; ethers, eg. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole and $\beta,\beta'$-dichlorodiethyl ether; nitrohydrocarbons, eg. nitromethane, nitroethane, nitrobenzene, o-, m- and p-chloronitrobenzene and o-nitrotoluene; aliphatic and cycloaliphatic hydrocarbons, eg. heptane, pinane, nonane, o-, m- and p-cymene, gasoline fractions boiling within a range of from $70°$ to $190°$ C., cyclohexane, methylcyclohexane, decalin, petroleum ether, hexane, naphtha, 2,2,4-trimethylpentane, 2,2,3-trimethylpentane, 2,3,3-trimethylpentane and octane; esters, eg. ethyl acetate, ethyl acetoacetate and isobutyl acetate; amides, eg. formamide, methylformamide and dimethylformamide; ketones, eg. acetone and methyl ethyl ketone; and corresponding mixtures. The solvent is advantageously used in an amount of from 100 to 2,000% by weight, preferably from 200 to 700% by weight, based on the starting materials.

Any subsequent alkylation is advantageously carried out in water or in an alcohol, eg. methanol, ethanol, n-propanol, i-propanol or butanol.

The acid acceptors used can be any of the conventional acid-binding agents. These preferably include tertiary amines, alkaline earth metal compounds, ammonium compounds and alkali metal compounds, as well as mixtures of these. However, zinc compounds may also be used. Specific examples of basic compounds which may be used are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, zinc acetate, sodium formate, sodium acetate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, diisopropylethylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N-methylpyrrolidone, N-ethylpyrrolidone, N-methylpiperidine, N-ethylpiperidine, N-methylpyrrolidine, N-ethylpyrrolidine, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, $\alpha$-picoline, $\beta$-picoline, $\gamma$-picoline, isoquinoline, pyrimidine, acridine, N,N,N',N'-tetramethylethylenediamine, N,N,N',N'-tetraethylethylenediamine, quinoxaline, quinazoline, N-propyldiisopropylamine, N,N'-dimethylcyclohexylamine, 2,6-lutidine, 2,4-lutidine, trifurylamine and triethylenediamine.

Where starting materials of the formulae VI and VII are employed, compounds which accelerate or initiate a cyclization reaction may be added, if appropriate.

Examples of suitable cyclizing agents are the inorganic acid acceptors mentioned above, and also, for example, sodium propionate, sodium butyrate, sodium isobutyrate, potassium formate, potassium acetate, potassium propionate, potassium butyrate, potassium isobutyrate, sodium methylate, sodium ethylate, sodium propylate, sodium isopropylate, sodium butylate, sodium isobutylate, sodium sec.-butylate, sodium tert.-butylate, sodium ethylene-glycolate, sodium 1,2-propylene-glycolate, sodium 1,3-propylene-glycolate, sodium diethyleneglycolate, sodium triethylene-glycolate, sodium 1,2-dipropylene-glycolate, potassium methylate, potassium ethylate, potassium n-propylate, potassium isopropylate, potassium n-butylate, potassium isobutylate, potassium sec.-butylate, potassium tert.-butylate, potassium ethylene-glycolate, potassium 1,2-propyleneglycolate, potassium 1,3-propylene-glycolate, potassium diethyleneglycolate, potassium triethylene-glycolate and potassium 1,2-dipropylene-glycolate.

The acid acceptor is advantageously employed in an equivalent amount to the starting material VI or VII, or in an excess of up to 20%.

The starting materials for the processes mentioned are known or can be prepared by known methods. Starting materials of the formulae V and VI are disclosed in German Laid-Open Application DOS No. 2,828,969 whilst starting materials VII are described in German Published Application DAS No. 1,259,871. The carbamyl chloride VIII is used in German Laid-Open Application DOS No. 2,650,014.

EXAMPLE 1

65.7 parts of N-methyl-N'-(3',4'-dichlorophenyl)-urea are suspended in 300 parts of dioxane. 42.5 parts of chlorosulfonyl isocyanate are added, a little at a time, at room temperature. After the mixture has been stirred for 16 hours, insoluble matter is filtered off and the solution is concentrated; residual solvent is removed at 40°–60° C./0.01 mbar. 90 parts of ethyl acetate are added to the residue and when the mixture has crystallized 200 ml of petroleum ether are added. The product is filtered off and dried, giving 75 parts of 2H-4-methyl-6-(3',4'-dichlorophenyl)-3,4,5,6-tetrahydro-1,2,4,6-thiatriazine-3,5-dione-1,1-dioxide (active ingredient 1), melting point 180°–183° C.

EXAMPLE 2

15.4 parts of chlorosulfonyl isocyanate are added, a little at a time, to a suspension of 20 parts of N-methyl-N'-(4'-chlorophenyl)-urea in 130 parts of dioxane at 35°–40° C. The mixture is stirred for 8 hours, 12 parts of triethylamine are added and the batch is stirred for a further 12 hours. The solution is then filtered and concentrated. 15 parts of a 30% strength sodium methylate solution are added to the residue; the methanol is then distilled off. Residual solvent can be removed at 50°–60° C./0.1 mbar. The residue is taken up in methylene chloride, the mixture is stirred for 1–2 hours and the precipitate is filtered off. 19 parts of 2-sodium-4-methyl-6-(4'-chlorophenyl)-3,4,5,6-tetrahydro-1,2,4,6-thiatriazine-3,5-dione-1,1-dioxide (active ingredient 2), melting point <240° C., are obtained.

EXAMPLE 3

43.8 parts of N-methyl-N'-(3',4'-dichlorophenyl)urea are introduced into 180 parts of dioxane and 28.3 parts of chlorosulfonyl isocyanate are added, a little at a time, at 12°–15° C., after which the mixture is stirred for 12 hours at room temperature.

20.2 parts of triethylamine are run in at from 10° to 12° C. and the batch is then stirred for 30 hours at room temperature. After filtering off undissolved material, the filtrate is concentrated under reduced pressure. 18 parts of 0.1 molar sodium methylate solution in methanol are added at from 0° to 5° C. and after stirring the mixture for 30 minutes, the precipitate is filtered off and dried. 42.1 parts of 2H-4-methyl-6-(3',4'-dichlorophenyl)-3,4,5,6-tetrahydro-1,2,4,6-thiatriazine-3,5-dione-1,1-dioxide, which crystallizes with about 0.5 mole of dioxane, are obtained; melting point <240° C. (active ingredient 3).

EXAMPLE 4

10 parts of active ingredient 1 are introduced into 100 ml of dry ethanol, 10.5 parts of a 2.9 molar sodium methylate solution in ethanol are added and the mixture is stirred for 15 minutes at room temperature. The solvent is distilled off and the residue is reprecipitated from ethyl acetate/petroleum ether, giving 10.3 parts of the sodium salt of 4-methyl-6-(3',4'-dichlorophenyl)-3,4,5,6-tetrahydro-1,2,4,6-thiatriazine-3,5-dione-1,1-dioxide (active ingredient 4), melting point <240° C.

EXAMPLE 5

22 parts of N-methyl-N'-(4'-chlorophenyl)sulfonediamide are introduced into 180 parts of toluene and 12.7 parts of chlorocarbonyl isocyanate are added, a little at a time, at 20°–25° C. The mixture is stirred for 1 hour at room temperature and then refluxed for 6 hours. It is filtered, the filtrate is concentrated and the product is precipitated with toluene/petroleum ether. The mixture is filtered and the filter residue is stirred into isopropanol; it contains 15.0 parts of pure 2-methyl-4H-6-(4'-chlorophenyl)-3,4,5,6-tetrahydro-1,2,4,6-thiatriazine-3,5-dione-1,1-dioxide (active ingredient 5), melting point 170°–172° C.

EXAMPLE 6

12.7 parts of chlorocarbonyl isocyanate are added, a little at a time, to 25.6 parts of N-isopropyl-N'-(4-chlorophenyl)-sulfonediamide and 18.0 parts of toluene at room temperature. The mixture is stirred for 1 hour at room temperature and 4 hours under reflux and is then filtered, and the product is precipitated with pentane. 26 parts of 2-isopropyl-4H-(4'-chlorophenyl)-3,4,5,6-tetrahydro-1,2,4,6-thiatriazine-3,5-dione-1,1-dioxide (active ingredient 6), melting point 130°–133° C., are obtained.

EXAMPLE 7

8.0 parts of active ingredient 5 (Example 6), 1.1 parts of sodium hydroxide, 30 parts of water and 25 parts of methanol are mixed. 7.7 parts of dimethyl sulfate are then added, a little at a time, at 25°–30° C. and the mixture is stirred for 3 hours at room temperature. 18 parts of concentrated aqueous ammonia solution are then added, the mixture is filtered and the filter residue is dried. 7.8 parts of 2,4-dimethyl-6-(4'-chlorophenyl)-3,4,5,6-tetrahydro-1,2,4,6-thiatriazine-3,5-dione-1,1-dioxide (active ingredient 7), melting point 82°–84° C., are obtained.

EXAMPLE 8

11.7 parts of N-methyl-N-isocyanatocarbonylsulfamyl chloride are introduced into 65 parts of absolute ether and 2.9 parts of isopropylamine are added, a little at a time, at from −50° C. to −55° C. The mixture is brought to room temperature and is then refluxed for 15 minutes. After stirring for 2 hours, the precipitate is filtered off. It is then dissolved in 2 N NaOH, the solution is extracted with methylene chloride, the aqueous phase is acidified with 2 N HCl and the precipitate is filtered off and dried. 2.2 parts of 2-methyl-4H-6-isopropyl-3,4,5,6-tetrahydro-1,2,4,6-thiatriazine-3,5-dione-1,1-dioxide (active ingredient 8), melting point 77°–80° C., are obtained.

The following were prepared by methods similar to Examples 1 to 8:

TABLE

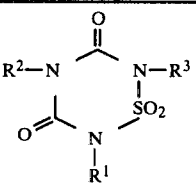

| Active ingredient no. | $R^1$ | $R^2$ | $R^3$ | M.p. (°C.) |
|---|---|---|---|---|
| 9 | $CH_3$ | H | –⟨O⟩ | 187–192 |
| 10 | " | Na | " | >240 |
| 11 | " | $CH_3$ | " | 121–125 |
| 12 | $C_2H_5$ | H | " | |
| 13 | " | Na | " | |
| 14 | i-$C_3H_7$ | H | " | 188–194 |
| 15 | " | Na | " | >240 |
| 16 | ⟨H⟩ | H | " | |
| 17 | " | Na | " | |
| 18 | H | $CH_3$ | –⟨O⟩–$OCH_3$ | |
| 19 | Na | " | " | |
| 20 | H | i-$C_3H_7$ | " | |
| 21 | Na | " | " | |
| 22 | $CH_3$ | " | " | |
| 23 | H | $CH_3$ | –⟨O⟩–$OCF_3$ | |
| 24 | Na | " | " | |
| 25 | H | i-$C_3H_7$ | " | |
| 26 | Na | " | " | |
| 27 | $CH_3$ | $CH_3$ | " | |
| 28 | H | $CH_3$ | –⟨O⟩–$CF_3$ | |
| 29 | Na | $CH_3$ | –⟨O⟩–$CF_3$ | |
| 30 | H | i-$C_3H_7$ | " | |
| 31 | Na | " | " | |
| 32 | $CH_3$ | $CH_3$ | " | |
| 33 | H | $CH_3$ | –⟨O⟩–CH(CH3)2 | |
| 34 | Na | $CH_3$ | " | |
| 35 | $HN(C_2H_5)_3$ | $CH_3$ | " | |
| 36 | H | i-$C_3H_7$ | " | |
| 37 | Na | i-$C_3H_7$ | " | |
| 38 | $HN(C_2H_5)_3$ | i-$C_3H_7$ | " | |
| 39 | $CH_3$ | H | " | 185 (decomposes) |
| 40 | $CH_3$ | Na | " | |
| 41 | i-$C_3H_7$ | H | " | 130–133 |
| 42 | i-$C_3H_7$ | Na | " | >240 |
| 43 | $CH_3$ | $CH_3$ | " | 77–79 |
| 44 | i-$C_3H_7$ | $CH_3$ | " | 120 (decomposes) |
| 45 | H | $CH_3$ | –⟨O⟩–+ | |

TABLE-continued

| Active ingredient no. | $R^1$ | $R^2$ | $R^3$ | M.p. (°C.) |
|---|---|---|---|---|
| 46 | Na | $CH_3$ | " | |
| 47 | $HN(C_2H_5)_3$ | " | " | |
| 48 | H | i-$C_3H_7$ | " | |
| 49 | Na | i-$C_3H_7$ | " | |
| 50 | $HN(C_2H_5)_3$ | i-$C_3H_7$ | " | |
| 51 | $CH_3$ | H | " | |
| 52 | $CH_3$ | Na | " | |
| 53 | i-$C_3H_7$ | H | " | |
| 54 | i-$C_3H_7$ | Na | " | |
| 55 | $CH_3$ | $CH_3$ | " | |
| 56 | i-$C_3H_7$ | $CH_3$ | " | |
| 57 | H | $CH_3$ | –⟨O⟩–$CF_3$ | |
| 58 | Na | $CH_3$ | " | |
| 59 | $HN(C_2H_5)_3$ | $CH_3$ | " | |
| 60 | H | i-$C_3H_7$ | " | |
| 61 | Na | i-$C_3H_7$ | " | |
| 62 | $HN(C_2H_5)_3$ | i-$C_3H_7$ | " | |
| 63 | $CH_3$ | H | " | |
| 64 | $CH_3$ | Na | " | |
| 65 | i-$C_3H_7$ | H | " | 130–135 |
| 66 | i-$C_3H_7$ | Na | " | 240 |
| 67 | $CH_3$ | $CH_3$ | " | |
| 68 | i-$C_3H_7$ | $CH_3$ | " | $n_D^{25}=1,4995$ |
| 69 | H | $CH_3$ | –⟨O⟩–F | |
| 70 | Na | $CH_3$ | " | |
| 71 | $HN(C_2H_5)_3$ | $CH_3$ | " | |
| 72 | H | i-$C_3H_7$ | " | |
| 73 | Na | i-$C_3H_7$ | " | |
| 74 | $HN(C_2H_5)_3$ | i-$C_3H_7$ | " | |
| 75 | $CH_3$ | H | " | |
| 76 | $CH_3$ | Na | " | |
| 77 | i-$C_3H_7$ | H | " | |
| 78 | i-$C_3H_7$ | Na | " | |
| 79 | $CH_3$ | $CH_3$ | " | |
| 80 | i-$C_3H_7$ | $CH_3$ | " | |
| 81 | H | $CH_3$ | –⟨O⟩–F | |
| 82 | Na | $CH_3$ | " | |
| 83 | $HN(C_2H_5)_3$ | $CH_3$ | " | |
| 84 | H | i-$C_3H_7$ | " | |
| 85 | Na | i-$C_3H_7$ | " | |
| 86 | $HN(C_2H_5)_3$ | i-$C_3H_7$ | " | |
| 87 | $CH_3$ | H | " | |
| 88 | $CH_3$ | Na | " | |
| 89 | i-$C_3H_7$ | H | " | |
| 90 | i-$C_3H_7$ | Na | " | |
| 91 | $CH_3$ | $CH_3$ | " | |
| 92 | i-$C_3H_7$ | $CH_3$ | " | |
| 93 | H | $CH_3$ | –⟨O⟩–F | |
| 94 | Na | $CH_3$ | " | |
| 95 | $HN(C_2H_5)_3$ | $CH_3$ | " | |
| 96 | H | i-$C_3H_7$ | " | |
| 97 | Na | i-$C_3H_7$ | " | |
| 98 | $HN(C_2H_5)_3$ | i-$C_3H_7$ | " | |

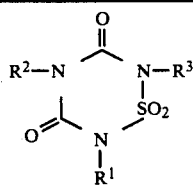

| Active ingredient no. | $R^1$ | $R^2$ | $R^3$ | M.p. (°C.) |
|---|---|---|---|---|
| 99 | $CH_3$ | H | " | |
| 100 | $CH_3$ | Na | " | |
| 101 | $i-C_3H_7$ | H | " | |
| 102 | $i-C_3H_7$ | Na | " | |
| 103 | $CH_3$ | $CH_3$ | " | |
| 104 | $i-C_3H_7$ | $CH_3$ | " | |
| 105 | H | $CH_3$ | 3,4-difluorophenyl | |
| 106 | Na | $CH_3$ | " | |
| 107 | $HN(C_2H_5)_3$ | $CH_3$ | " | |
| 108 | H | $i-C_3H_7$ | " | |
| 109 | Na | $i-C_3H_7$ | " | |
| 110 | $HN(C_2H_5)_3$ | $i-C_3H_7$ | " | |
| 111 | $CH_3$ | H | " | |
| 112 | $CH_3$ | Na | " | |
| 113 | $i-C_3H_7$ | H | " | |
| 114 | $i-C_3H_7$ | Na | " | |
| 115 | $CH_3$ | $CH_3$ | " | |
| 116 | $i-C_3H_7$ | $CH_3$ | " | |
| 117 | H | $CH_3$ | 3-chlorophenyl | |
| 118 | Na | $CH_3$ | " | |
| 119 | $HN(C_2H_5)_3$ | $CH_3$ | " | |
| 120 | H | $i-C_3H_7$ | " | |
| 121 | Na | $i-C_3H_7$ | " | |
| 122 | $HN(C_2H_5)_3$ | $i-C_3H_7$ | " | |
| 123 | $CH_3$ | H | " | 160 (decomposes) |
| 124 | $CH_3$ | Na | " | |
| 125 | $i-C_3H_7$ | H | " | |
| 126 | $i-C_3H_7$ | Na | " | |
| 127 | $CH_3$ | $CH_3$ | " | |
| 128 | $i-C_3H_7$ | $CH_3$ | " | |
| 129 | H | $CH_3$ | 4-chlorophenyl | 130–135 |
| 130 | $HN(C_2H_5)_3$ | $CH_3$ | " | |
| 131 | H | $i-C_3H_7$ | " | |
| 132 | Na | $i-C_3H_7$ | " | |
| 133 | $HN(C_2H_5)_3$ | $i-C_3H_7$ | " | |
| 134 | $CH_3$ | Na | " | |
| 135 | $i-C_3H_7$ | Na | " | |
| 136 | $i-C_3H_7$ | $CH_3$ | " | |
| 137 | H | $CH_3$ | 3,4-dichlorophenyl | |
| 138 | Na | $CH_3$ | " | |
| 139 | $HN(C_2H_5)_3$ | $CH_3$ | " | |
| 140 | H | $i-C_3H_7$ | " | |
| 141 | Na | $i-C_3H_7$ | " | |
| 142 | $HN(C_2H_5)_3$ | $i-CC_3H_7$ | " | |
| 143 | $CH_3$ | H | " | |
| 144 | $CH_3$ | Na | " | |
| 145 | $i-C_3H_7$ | H | " | |
| 146 | $i-C_3H_7$ | Na | " | |
| 147 | $CH_3$ | $CH_3$ | " | |
| 148 | $i-C_3H_7$ | $CH_3$ | " | |

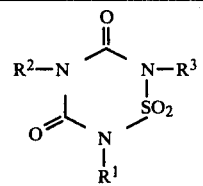

| Active ingredient no. | $R^1$ | $R^2$ | $R^3$ | M.p. (°C.) |
|---|---|---|---|---|
| 149 | $NH_4$ | " | 3,4-dichlorophenyl | |
| 150 | H | $C_2H_5$ | " | |
| 151 | Na | " | " | |
| 152 | H | $n-C_3H_7$ | " | |
| 153 | Na | " | " | |
| 154 | H | $i-C_3H_7$ | " | |
| 155 | Na | " | " | |
| 156 | $NH_4$ | " | " | |
| 157 | $HN(C_2H_5)_3$ | " | " | |
| 158 | H | $n-C_4H_9$ | " | |
| 159 | Na | " | " | |
| 160 | H | $i-C_4H_9$ | " | |
| 161 | Na | " | " | |
| 162 | H | sek.-$C_4H_9$ | " | |
| 163 | Na | " | " | |
| 164 | H | $t-C_4H_9$ | " | |
| 165 | Na | " | " | |
| 166 | H | phenyl | " | |
| 167 | $CH_3$ | H | " | 168–172 |
| 168 | " | Na | " | |
| 169 | $C_2H_5$ | H | " | |
| 170 | " | Na | " | |
| 171 | $i-C_3H_7$ | H | " | 120–122 |
| 172 | " | Na | " | 240 |
| 173 | $CH_3$ | $CH_3$ | " | 92 (decomposes) |
| 174 | $i-C_3H_7$ | $CH_3$ | " | 96–98 |
| 175 | H | $CH_3$ | 3-chloro-4-fluorophenyl | 146–148 |
| 176 | Na | $CH_3$ | " | |
| 177 | $HN(C_2H_5)_3$ | $CH_3$ | " | |
| 178 | H | $i-C_3H_7$ | " | |
| 179 | Na | $i-C_3H_7$ | " | |
| 180 | $HN(C_2H_5)_3$ | $i-C_3H_7$ | " | |
| 181 | $CH_3$ | H | " | |
| 182 | $CH_3$ | Na | " | |
| 183 | $i-C_3H_7$ | H | " | |
| 184 | $i-C_3H_7$ | Na | " | |
| 185 | $CH_3$ | $CH_3$ | " | |
| 186 | $i-C_3H_7$ | $CH_3$ | " | |
| 187 | H | $CH_3$ | 3-chloro-4-methoxyphenyl | |
| 188 | Na | $CH_3$ | " | |
| 189 | $HN(C_2H_5)_3$ | $CH_3$ | " | |
| 190 | H | $i-C_3H_7$ | " | |
| 191 | Na | $i-C_3H_7$ | " | |
| 192 | $HN(C_2H_5)_3$ | $i-C_3H_7$ | " | |
| 193 | $CH_3$ | H | " | |
| 194 | $CH_3$ | Na | " | |
| 195 | $i-C_3H_7$ | H | " | |
| 196 | $i-C_3H_7$ | Na | " | |
| 197 | $CH_3$ | $CH_3$ | " | |
| 198 | $i-C_3H_7$ | $CH_3$ | " | |

TABLE-continued $$R^2-N \overset{\overset{O}{\|}}{\underset{\underset{\underset{R^1}{|}}{N}}{\underset{|}{\bigtriangleup}}} \overset{N-R^3}{\underset{SO_2}{}}$$

| Active ingredient no. | R¹ | R² | R³ | M.p. (°C.) |
|---|---|---|---|---|
| 199 | H | CH₃ | —⟨○⟩—Br, Cl | |
| 200 | Na | CH₃ | " | |
| 201 | HN(C₂H₅)₃ | CH₃ | " | |
| 202 | H | i-C₃H₇ | " | |
| 203 | Na | i-C₃H₇ | " | |
| 204 | HN(C₂H₅)₃ | i-C₃H₇ | —⟨○⟩—Br, Cl | |
| 205 | CH₃ | H | " | |
| 206 | CH₃ | Na | " | |
| 207 | i-C₃H₇ | H | " | |
| 208 | i-C₃H₇ | Na | " | |
| 209 | CH₃ | CH₃ | " | |
| 210 | i-C₃H₇ | CH₃ | " | |
| 211 | H | CH₃ | —⟨○⟩—CH₃, Cl | |
| 212 | Na | CH₃ | " | |
| 213 | HN(C₂H₅)₃ | CH₃ | " | |
| 214 | H | i-C₃H₇ | " | |
| 215 | Na | i-C₃H₇ | " | |
| 216 | HN(C₂H₅)₃ | i-C₃H₇ | " | |
| 217 | CH₃ | H | " | |
| 218 | CH₃ | Na | " | |
| 219 | i-C₃H₇ | H | " | |
| 220 | i-C₃H₇ | Na | " | |
| 221 | CH₃ | CH₃ | " | |
| 222 | i-C₃H₇ | CH₃ | " | |
| 223 | H | CH₃ | —⟨○⟩—Br | |
| 224 | Na | CH₃ | " | |
| 225 | HN(C₂H₅)₃ | CH₃ | " | |
| 226 | H | i-C₃H₇ | " | |
| 227 | Na | i-C₃H₇ | " | |
| 228 | HN(C₂H₅)₃ | i-C₃H₇ | " | |
| 229 | CH₃ | H | " | |
| 230 | CH₃ | Na | " | |
| 231 | i-C₃H₇ | H | " | |
| 232 | i-C₃H₇ | Na | —⟨○⟩—Br | |
| 233 | CH₃ | CH₃ | " | |
| 234 | i-C₃H₇ | CH₃ | " | |

Application may be effected for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below:

I. 90 parts by weight of the compound of Example 1 is mixed with 10 parts by weight of N-methyl-α-pyrrolidone. A mixture is obtained which is suitable for application in the form of very fine drops.

II. 20 parts by weight of the compound of Example 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 14 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 33 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 69 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 37 is intimately mixed with 97 parts by weight of particulate kaolin. A dust is obtained containing 3% by weight of the active ingredient.

VII. 30 parts by weight of compound no. 66 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 72 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or agents may be applied pre- or postemergence, i.e., before unwanted plants have germinated from seed or sprouted from vegetative plant parts, or to the leaves of unwanted and crop plants. Preferably, the new active ingredients are applied after emergence of the unwanted plants, both to cropland and uncropped land.

If the crop plants tolerate the active ingredients less well, application techniques may be used in which the agents are sprayed frrom suitable equipment in such a manner that the leaves of sensitive crop plants are if possible not touched, and the agents reach the soil or the unwanted plants growing beneath the crop plants (post-directed, lay-by treatment).

Depending on the season and the growth stage of the plants, the application rates of active ingredient are from 0.1 to 15 kg/ha and more, the higher rates being particularly suitable for the total elimination of vegetation.

The influence of various representatives of the compounds according to the invention on the growth of unwanted plants is demonstrated in greenhouse experiments, in which prior art compounds were used for comparison purposes.

The vessels employed were plastic flowerpots having a volume of 300 cm$^3$, and which were filled with a sandy loam containing about 1.5% humus. The seeds of the test plants given in Table 1 were sown shallow, and separately, according to species.

TABLE 1

| | List of plant names | |
|---|---|---|
| Botanical name | Abbreviation in table | Common name |
| Abutilon theophrasti | Abutilon theophr. | velvet leaf |
| Beta vulgaris | — | sugarbeet |
| Chenopodium album | — | lambsquarters |
| Chrysanthemum segetum | Chrysanthemum seg. | corn marigold |
| Centaurea cyanus | Centaurea cyan. | cornflower |
| Gossypium hirsutum | — | cotton |
| Matricaria spp. | Matric. spp. | chamomile |
| Nicandra physaloides | Nicandra physal. | apple-of-Peru |
| Sinapis alba | — | white mustard |
| Solanum nigrum | Solanum nigr. | black nightshade |
| Sorghum bicolor | — | sorghum |
| Triticum aestivum | — | wheat |
| Zea mays | — | Indian corn |

In the preemergence treatment, the active ingredients were immediately applied to the surface of the soil as a suspension or emulsion in water by spraying through finely distributing nozzles. The amount of active ingredient applied in this treatment was equivalent to 2.0 kg/ha.

After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals.

For the postemergence treatment, the plansts were first grown in the vessels to a height of from 3 to 10 cm, depending on growth form, before being treated. For this treatment, either plants which were sown directly in the pots and grew there were selected, or plants which were grown separately as seedlings and transplanted to the experiment vessels a few days before treatment. The amount of active ingredient applied in this treatment was equivalent to 1.0 kg/ha.

No cover was placed on the vessels. The pots were set up in the greenhouse-species from warmer areas at from 20° to 30° C., and species from moderate climates at 15° to 30° C. The experiments were run for from 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The substance used for comparison purposes was 2,4-diisopropyl-3,4,5,6-tetrahydro-1,2,4,6-thiatriazin- (3,5)-dione-1,1-dioxide (I) (U.S. Pat. No. 3,435,031). This compound was applied at a rate of 1.0 kg/ha.

In these experiments, for instance the active ingredient of Example 175 had, at 2 kg/ha, a considerable herbicidal action when applied preemergence.

The greenhouse experiments further revealed that postemergence treatment for example with the active ingredient of Example 4 (at 1.0 kg/ha) resulted in a selective herbicidal action superior to that obtained with I. The same is true of the active ingredient of Example 43.

It may also be useful to apply the active ingredients, either alone or in combination with other herbicides, in admixture with other crop protection agents, e.g., agents for combating pests or phytopathogenic fungi or bacteria. The compounds may also be mixed with solutions of mineral matters used to remedy nutritional or trace element deficiencies. Wetting agents, spreader-stickers and non-phytotoxic oils and oil concentrates may be added to initiate the herbicidal action.

We claim:

1. A 3,4,5,6-tetrahydro-thiatriazine-3,5-dione-1,1-dioxide of the formula

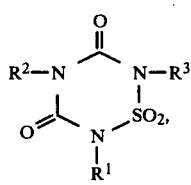

where $R^1$ is hydrogen, $R^2$ is alkyl of 1 to 4 carbon atoms and $R^3$ is halogen- or, haloalkyl-substituted phenyl.

2. A herbicide consisting essentially of a carrier and a tetrahydrothiatriazine-3,5-dione-1,1-dioxide of the formula I as claimed in claim 1.

3. A process for combating the growth of unwanted plants, wherein the plants or the soil are treated with a herbicidally effective amount of a tetrahydro-thiatriazine-3,5-dione-1,1-dioxide of the formula I as claimed in claim 1.

* * * * *